(12) United States Patent
Jarboe et al.

(10) Patent No.: US 7,748,294 B2
(45) Date of Patent: Jul. 6, 2010

(54) DEVICE FOR TATTOOING AND METHOD OF USING THE SAME

(76) Inventors: Adam P. Jarboe, 7028 Frank Ott Rd., Georgetown, IN (US) 47122; Jonathon M. Fruchte, 679 Timber Walk Dr., Simpsonville, SC (US) 29681; Megan B. Fruchte, 679 Timber Walk Dr., Simpsonville, SC (US) 29681; Brooks D. Borchers, 2650 University Ave. W. #103, St. Paul, MN (US) 55114; Joseph Gland, 3901 Lakehouse Rd., Apt. 04, Beltsville, MD (US) 20705; Kevin K. Hirako, 5009 Somam Ave., San Diego, CA (US) 92110; Samantha J. Vaitkunas, 1732 N. 9th St., Apt 28, Lafayette, IN (US) 47904; Katherine Christensen, 14920 Yolanda La., Manassas, VA (US) 20112; Lon Farr, 8450 E. Old Spanish Trail, Unit 256, Tucson, AZ (US) 85710; John Joseph Rudolphi, 281 Ruby Rd., Noble, IL (US) 62868; Jesseca R. Zapf, 461 Redwood Dr., Pendleton, IN (US) 46064

( * ) Notice: Subject to any disclaimer, the term of this patent is extended or adjusted under 35 U.S.C. 154(b) by 0 days.

(21) Appl. No.: 11/867,706

(22) Filed: Oct. 5, 2007

(65) Prior Publication Data
US 2009/0090218 A1    Apr. 9, 2009

(51) Int. Cl.
B43K 5/00    (2006.01)
A61B 17/34    (2006.01)
(52) U.S. Cl. .................. 81/9.22; 30/362; 606/186
(58) Field of Classification Search .......... 81/9.22; 30/362; 606/186
See application file for complete search history.

(56) References Cited

U.S. PATENT DOCUMENTS

| 464,801 | A | | 12/1891 | O'Reilly | |
|---|---|---|---|---|---|
| 4,159,659 | A | * | 7/1979 | Nightingale | 81/9.22 |
| 4,204,438 | A | | 5/1980 | Binaris et al. | |
| 4,719,825 | A | | 1/1988 | LaHaye et al. | |
| 4,862,772 | A | * | 9/1989 | Piperato | 81/9.22 |
| 4,914,988 | A | | 4/1990 | Chang | |
| 5,054,339 | A | * | 10/1991 | Yacowitz | 81/9.22 |
| 5,279,552 | A | | 1/1994 | Magnet | |
| 5,471,102 | A | | 11/1995 | Becker et al. | |
| 5,741,290 | A | | 4/1998 | Hsieh | |
| 6,033,421 | A | | 3/2000 | Theiss et al. | |
| 6,263,762 | B1 | * | 7/2001 | Zeitler | 81/9.22 |
| 6,345,553 | B1 | | 2/2002 | Adler et al. | |
| 6,352,546 | B1 | | 3/2002 | Hill | |
| 6,505,530 | B2 | | 1/2003 | Adler et al. | |

(Continued)

*Primary Examiner*—David B Thomas
(74) *Attorney, Agent, or Firm*—Lafkas Patent LLC; David M. Lafkas; Matthew E. Vale

(57) ABSTRACT

The present invention relates to a tattoo device having a single DC coil with a pulse width modulation (PWM) circuit to control when the single DC coil is energized. Such arrangement eliminates the need for a set screw as in traditional tattoo machines and allows for a lighter device having fewer vibrations, better balance, and improved precision when being used.

12 Claims, 3 Drawing Sheets

U.S. PATENT DOCUMENTS

| | | |
|---|---|---|
| 6,626,927 B1 | 9/2003 | Koplen |
| 6,897,756 B2 * | 5/2005 | Haisch ........................ 336/130 |
| 6,950,004 B2 * | 9/2005 | Godoy et al. ................. 336/160 |
| 7,025,774 B2 | 4/2006 | Freeman et al. |
| 7,207,242 B1 * | 4/2007 | Daigle ........................ 81/9.22 |
| 2007/0028722 A1 | 2/2007 | Vecchi |
| 2007/0083223 A1 | 4/2007 | Kluge |
| 2007/0107625 A1 | 5/2007 | Anderson et al. |

\* cited by examiner

Prior Art

DEVICE FOR TATTOOING AND METHOD OF USING THE SAME

CROSS-REFERENCE TO RELATED APPLICATION

Not applicable

STATEMENT REGARDING FEDERALLY SPONSORED RESEARCH

Not applicable.

NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND ON THE INVENTION

1. Field of the Invention

The present invention relates generally to tattooing, and more particularly relates to an ergonomic device and method for applying one or more tattoos to biological tissue.

2. Description of the Related Art

Tattooing is a widespread and a widely practiced body decoration technique. There are approximately 49,000 tattoo artists in the United States. The art and associated industry of tattooing is continuing to grow and expand throughout the United States and world.

In recent years, tattooing has spread beyond the commonly thought realm of body decoration and has been accepted into the aesthetic and cosmetic fields in the form of so-called "permanent makeup." Permanent makeup is most often associated with tattooing parts of the face, for example, eyebrows, eye line, lips, etc. Such permanent makeup may be a replacement for traditional cosmetic products and/or to assist in correcting physical shortcomings or defects.

To perform these techniques, it is known to use devices commonly known as tattoo machines, which have an elongated hollow body that can be maneuvered manually and is suitable to contain a coloring liquid and to act as a guide for one or more needles.

Tattoo machines have been in use for years. Commonly, one end of the elongated hollow body is provided with an exit hole for the liquid, inside which the needle can slide in a reciprocating fashion between two end positions, i.e., a position in which it is fully inserted within the hollow body and a position in which the tip of the needle protrudes from the hole in order to penetrate the skin and entrain the coloring liquid with it.

The reciprocating needle moves up and down and may puncture the biological tissue at the rate ranging from about 50 to about 300 times a second. Such sterilized needles may be installed in the machine and dipped in ink, which is introduced into the needles through capillary action. Some machines use needles connected to ink reservoirs rather than dipping the needle into ink.

Commonly, a tattoo machine uses an up-and-down motion to pierce the top layer of the biological tissue and therein drive insoluble, micrometer-sized particles of ink into the dermal layer of the biological tissue. The dermal layer is often about one-eighth inch deep.

Motor means are generally fitted on the hollow body and drive the needle between the two end positions, imparting thereto a vibrating motion. That is, as the needle makes sudden and immediate changes in direction, a great amount of vibrational energy is imparted to an individual maneuvering the tattoo machine.

Such vibrational energy may cause difficulty in properly manipulating the direction of the tattoo machine and may cause physical exhaustion and damage to muscles, ligaments, joints, and nerves of the individual maneuvering the tattoo machine. In the short term, this vibrational energy exerted upon the artist limits the number and length of sessions that an artist may devote to providing tattoos. In the long term, tattoo artists tend to develop carpel tunnel syndrome and/or osteoarthritis. In both the short term and long term, these disadvantages ultimately lead to less time to devote to the art and less revenue generation.

In addition to possible physical damage to an individual manipulating a standard tattoo machine, the vibrational energy of a standard tattoo machine allows for less control over the actual machine by an individual. Furthermore, the vibrational energy may cause the actual ink injected by the machine to not be as accurately or precisely placed under the skin, thereby allowing blurring of the image being created.

The motor means are activated not only to allow the needle to penetrate the skin while making the tattoo but also to fill the hollow body with the required coloring liquid; the hole for the exit of the liquid from the hollow body is in fact commonly used also as an inlet, and filling is performed generally by capillary action by dipping the end of the hollow body provided with the hole in a container that contains the pigment and by moving the needle in order to facilitate its drawing.

In addition to the vibrational drawbacks, most motor means have substantial dimensions that considerably increase the weight of the hollow body, accordingly limiting its maneuverability and easy handling.

Thus, what is desired is an ergonomic tattoo machine being comfortable to hold, having significantly less weight, and having less vibration.

SUMMARY

The various exemplary embodiments herein include an ergonomic device for tattooing biological tissue. The device is comprised of a body support, a hollow hand grip, a single direct current (DC) coil, a controlling means, an armature bar, a magnet, and a needle. The body support is comprised of a substantially planar section and an elevated section. The hollow hand grip is attached to a bottom side of the planar section, and the hollow hand grip has at least a first opening and a second opening such that each opening is opposed and connected to one another. The single DC coil is attached on a topside of the planar section. The controlling means is connected to the DC coil and is for controlling the direction of current through the DC coil and determining and setting the speed and strength at which the current through the DC coil changes direction. The armature bar is connected to the body support. The armature bar has a first end and a second end such that the first end is connected to the elevated section of the body support and the second end has a needle support. The magnet is attached to an underside of the armature bar and adjacent to the topside of the single DC coil. The needle is held at a head by the needle support and is directed towards the body support and through the first opening and second opening of the hollow hand grip.

BRIEF DESCRIPTION OF THE DRAWINGS

The various exemplary embodiments of the present invention, which will become more apparent as the description proceeds, are described in the following detailed description in conjunction with the accompanying drawings, in which.

DESCRIPTION OF THE REFERENCED NUMERALS

Figure 1:
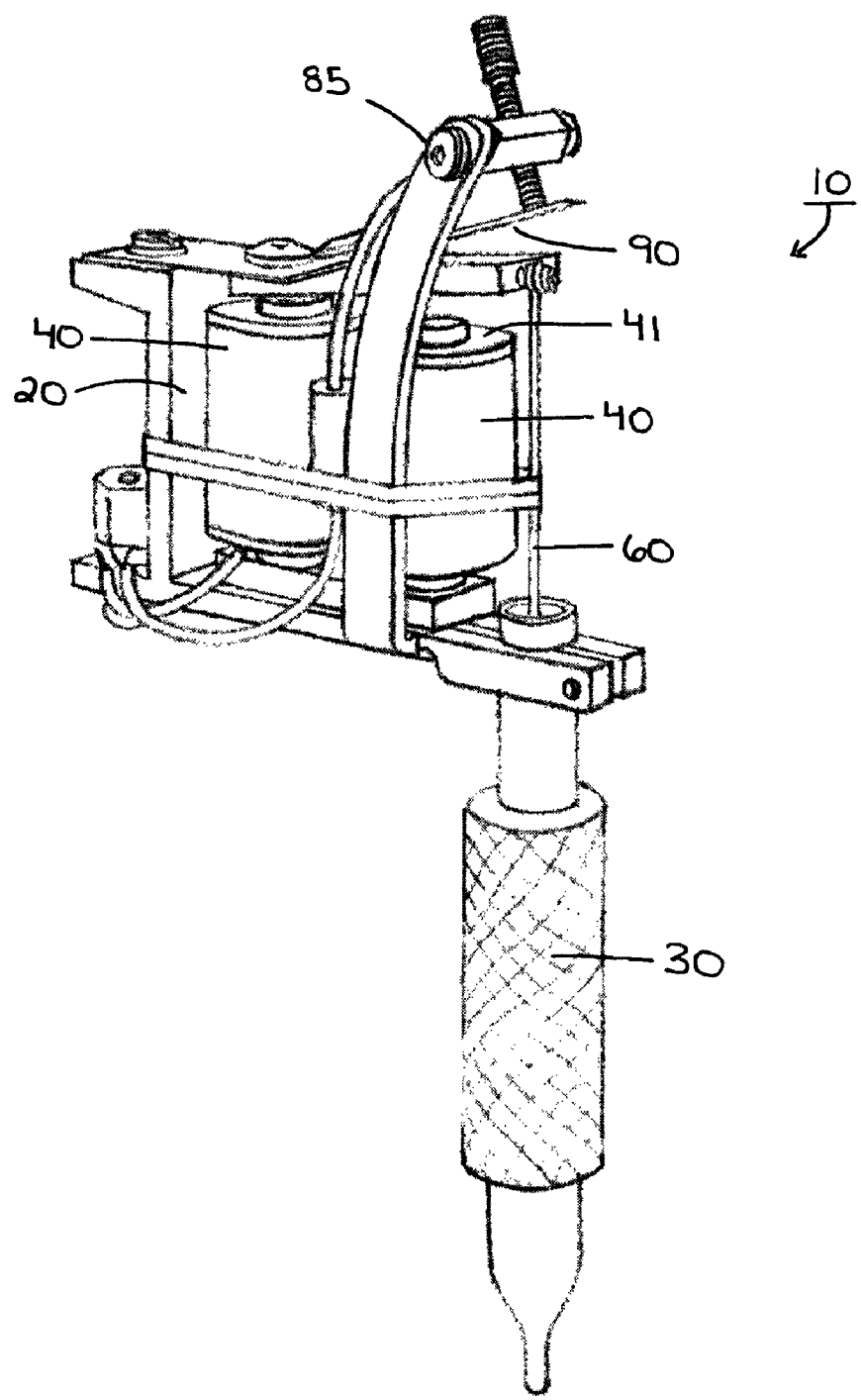
FIG. 1 illustrates the tattoo machine of the prior art.
Figure 2:
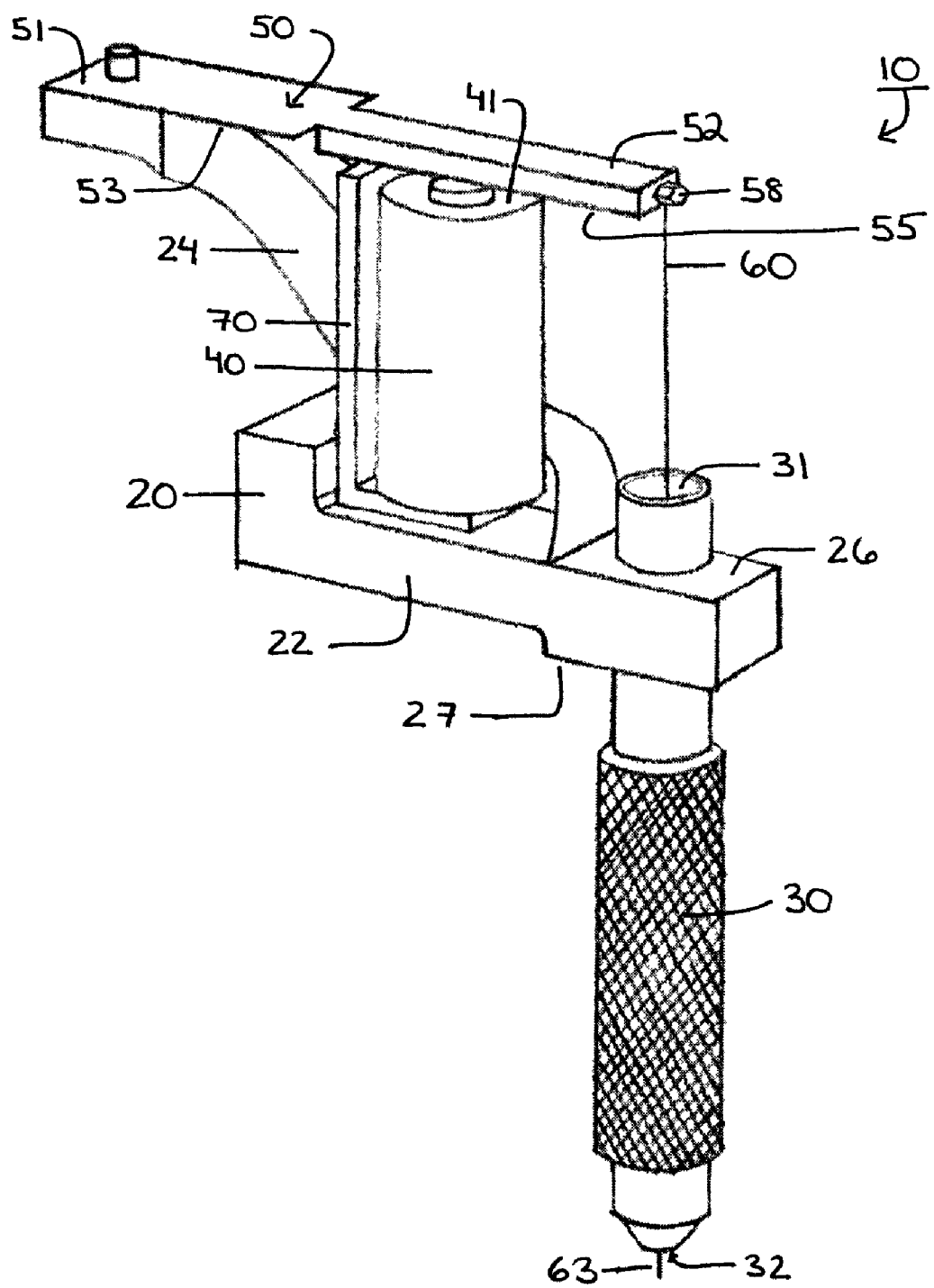
FIG. 2 illustrates an exemplary embodiment of the present invention.
Figure 3:
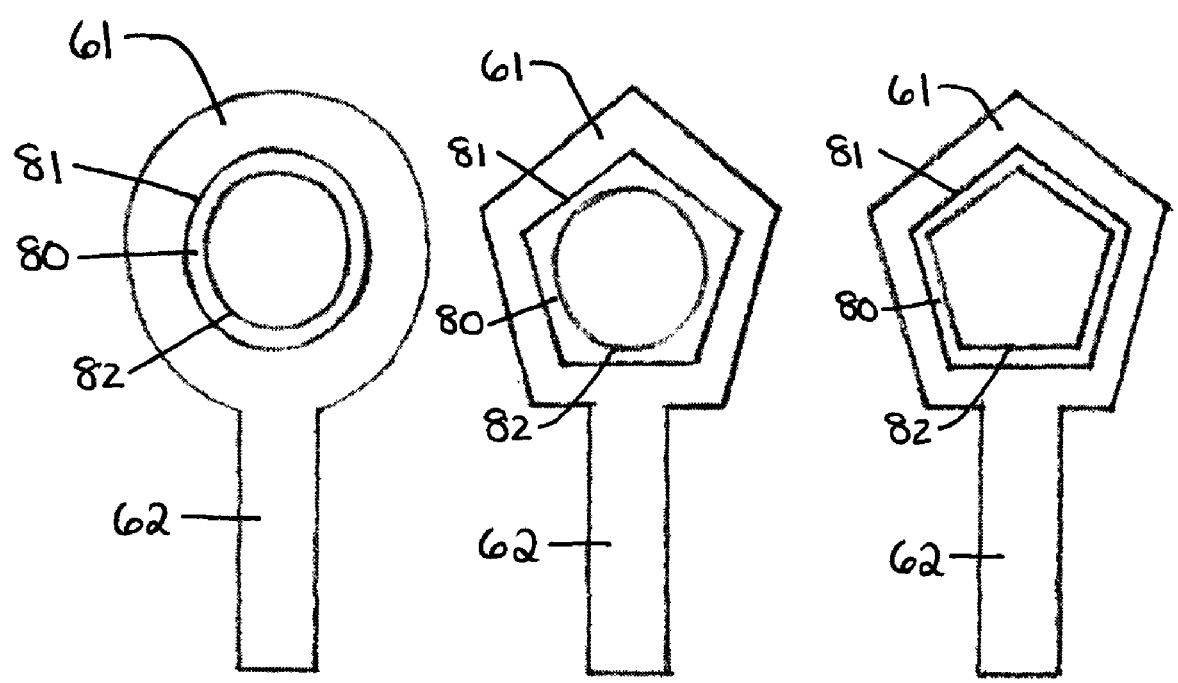
FIG. 3 illustrates an exemplary embodiment of needle heads according to the present invention.

In reference to the drawings, similar reference characters denote similar elements throughout all the drawings. The following is a list of the reference characters and associated element:

| | |
|---|---|
| 10 | tattoo device |
| 20 | body support |
| 22 | planar section |
| 24 | elevated section |
| 26 | top side |
| 27 | bottom side |
| 30 | hollow hand grip |
| 31 | first opening |
| 32 | second opening |
| 40 | DC coil |
| 41 | top end |
| 50 | armature bar |
| 51 | first end |
| 52 | second end |
| 53 | underside |
| 55 | magnet |
| 58 | needle support |
| 60 | needle |
| 61 | head |
| 62 | shaft |
| 63 | point |
| 70 | magnetic flux guide |
| 80 | grommet |
| 81 | outer perimeter |
| 82 | inner perimeter |
| 85 | set screw |
| 90 | spring |

DETAILED DESCRIPTION

As illustrated in FIG. 1, the various exemplary embodiments of the present invention are a device 10 for tattooing biological tissue. The device is comprised of a body support 20. In the exemplary embodiment represented herein, the body support has a substantially planar section 22 connected to an elevated section 24.

In the various exemplary embodiments, the planar section 22 of the body support 20 has a top side 26 and a bottom side 27. It is preferred that the elevated section be connected to the planar section such that the elevated section is directed away from the planar section on the top side.

The body support may be comprised of metals such as, for example, aluminum, steel, iron, brass, or the like. The body support may also be comprised of alloys, composites, or ceramics. The body support may be further colored and/or decorated to allow for customization and enhancement of the device's aesthetic appeal.

In the various exemplary embodiments, a hollow hand grip is connected to the bottom side of the planar section of the body support. In a preferred embodiment, the hollow hand grip 30 is substantially perpendicular to the planar section of the body support.

The hollow hand grip is preferably substantially cylindrical and elongated. The outer portion of the hollow hand grip may be surrounded by molded rubber, molded plastic, or formed metal (not shown) to allow for a more comfortable and natural grip by a single hand. The hollow hand grip may be removable and interchangeable with other hollow hand grips based upon the desires and/or needs of the individual manipulating the associated tattoo machine.

The hollow hand grip includes at least two openings; the first opening 31 is at the end of the hollow hand grip adjacent to the planar section. The first opening includes a similarly shaped opening through the planar section. In a preferred embodiment, the hollow hand grip extends through the planar section such that the planar section appears to have an opening. The second opening 32 of the hollow hand grip is at the opposing end of the hollow hand grip from the first opening such that the hollow hand grip appears to have a tunnel through it.

In the various exemplary embodiments, the device is further comprised of a single direct current (DC) coil 40. The single DC coil is positioned and attached to the top side of the planar section of the body support. The single DC coil may surround and rest upon a magnetic flux guide stand 70. The magnetic flux guide stand may be substantially "U" shaped and rest on the top side of the planar section of the body support. The magnetic flux guide is preferably made of a single contiguous material such as, for example, iron, nickel, or magnetite. It is preferred that the magnetic flux guide have a large cross-sectional area near an armature bar 50.

In the various exemplary embodiments, an armature bar 50 is connected to the body support on the elevated section. The armature bar is preferably connected to the elevated section substantially near the end furthest from the planar section. The armature bar has a first end 51 and a second end 52. The armature bar is connected at first end to the elevated section. A magnet 55 is connected to an underside 53 the armature bar between the first end and the second end. The magnet adjacent to a top end 41 of the DC coil. The second end of the armature bar includes a needle support 58.

A needle 60 is positioned and held by the needle support. A head 61 of the needle is held by the needle support. The shaft 62 and point 63 of the needle are directed towards the planar section of the body support and through the first opening of the hollow hand grip and through the second opening of the hollow hand grip.

Typically, the head of needles used for tattoo devices are circular in shape. Thus, the associated needle support needs to be substantially cylindrical in shape in order to fit inside and hold the head of the needle.

In an exemplary embodiment of the present invention, the head of the needle may be of any non-geometric or geometric shape, for example, a triangle, a square, a pentagon, a hexagon, etc. Different shapes of heads of needles may be used by an artist for various reasons such as, tracking the number of needles used on a particular individual, tracking the number of needles used in a particular day, identifying different shapes of heads of needles with various colors, etc.

When the head of the needle is a shape other than the typical circle shape, the corresponding needle support should correspond with the shape of the needle head. However, if a needle is for example, a pentagon, and a tattoo device has a circular needle support, a grommet 80 having an outer perimeter 81 and inner perimeter 82 may be used. It is preferred that the outer perimeter of the grommet is similar to the head of the needle and the inner perimeter is similar to the needle support. Thus, in the foregoing example, the outer perimeter of the grommet should be a pentagon and the inner perimeter should be a circle.

The shaft and point of the needle may be substantially hollow.

The single DC coil is connected to a controlling means 50. The controlling means sets the direction of current through the DC coil, and determine and sets the speed and strength at which the current through the DC coil changes direction.

As the DC coil changes current direction, the magnet connected to the armature bar is either attracted or repelled by the DC coil depending on the direction of the current. As the magnetic is attracted, the armature bar is brought towards the body support, thus driving the attached needle downward. As the magnet is repelled, the armature bar is moved away from the body support, thus driving the attached needle upward. In addition to actually being repelled, the armature bar connected to the magnet is trying to return to its natural resting point.

The device is connected to a power supply in the form of, for example, a 120V AC wall outlet or connected battery.

In an exemplary embodiment, an AC-DC power supply may be connected to such wall outlet and converting an output of 7-18V DC. The 7-18V DC signal is then reduced to 5V DC using a voltage regulator. The reduced signal is then used to power a circuit which utilizes two 555 timers to change the frequency and pulse width of the voltage into the single DC coil, thus changing the performance characteristics of the machine to an individual's requirements.

In a preferred embodiment, the controlling means for directing the DC coil uses a pulse width modulation (PWM) circuit to control when the single DC coil is energized. An individual may select a desired pulse width by varying a potentiometer.

The PWM circuit functions by taking in a normally high (5V DC) trigger signal. Whenever the trigger is dropped to a low (0V DC) value, the control signal will send a pulse. Dependant on the position of the potentiometer, the pulse will have a varying width. For this design, the trigger operates at a given frequency. Thus, it creates pulses at a regular interval. By adjusting the width of each pulse, the frequency of the output will not change, but the pulse width will.

As the DC coil in the various exemplary embodiments herein can be energized longer than a standard mechanical switch as in typical tattoo devices, the present invention needs only a single DC coil. The amount of associated energy thus delivered to the needle by the single DC coil of the present invention can be approximated as W=Fdx where W is the energy imparted to the needle by the single DC coil, F is the net force acting on the needle, and dx is the distance that the needle traverses while the DC coil is energized.

The above-mentioned force (F) can be calculated as $F=(mN^2I^2A)/2L$ where m is the permittivity of free space, N is the number of turns in the coil, I is the current flowing through the coil, A is the surface area of the top of the magnetic flux guide, and L is the average distance between the armature bar and the magnetic flux guide.

Using the above calculations shows that keeping the single DC coil of the present invention turned on four times longer than the coils of a traditional tattoo machine results in the impartation of the same amount of energy but with half the number of coil windings in the present invention.

The present invention eliminates the need for a set screw as in the prior art. The set screw of the prior art design is a mechanical arrangement for determining how far the needle moves and at what speed. Elimination of the screw set allows for elimination of excess weight which allows for improved safety, balance, and use of the machine. Most importantly, however, elimination of the screw set as in the present invention allows for a substantial decrease in the vibrational energy, thereby allowing for longer and more comfortable use of the machine while also allowing for more accurate and precise manipulation of the machine.

As the spring of the prior art moves upward, the needle moves upward. However, as the spring contacts the set screw, the coils are energized thereby pulling the spring and needle downward. The coils are turned off when the spring no longer is in contact with the set screw. Based on the positioning of the set screw, the spring and needle speed up or slow down.

Such prior art design creates a great amount of vibration between the spring and the set screw contacting. The present invention does not use a set screw and thereby is able to substantially limit the amount of vibrational energy transferred to an individual holding the device.

It is preferred that the single DC coil be positioned as closely to the first opening of the hollow hand grip as possible. Positioning the single DC coil in such manner significantly increases balance of the device and reduces vibrational energy.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

What is claimed is:

1. An ergonomic device for tattooing biological tissue, the device being comprised of:
    a body support comprised of a substantially planar section and an elevated section;
    a hollow hand grip attached to a bottom side of the planar section, the hollow hand grip having at least a first opening and a second opening, each opening opposed and connected to one another;
    a single DC coil on a topside of the planar section;
    a controlling means connected to the DC coil for controlling the direction of current through the DC coil, and determining and setting the speed and strength at which the current through the DC coil changes direction;
    an armature bar connected to the body support, wherein the armature bar has a first end and a second end, the first end connected to the elevated section of the body support and the second end having a needle support;
    a magnetic flux guide connected to the top side of the planar section and a portion of which is surrounded by the single DC coil;
    a magnet attached to an underside of the armature bar and adjacent to the topside of the single DC coil;
    a needle held at a head by the needle support and directed towards the body support and through the first opening and second opening of the hollow hand grip, wherein the head of the needle and the needle support are of different shape; and
    a grommet having an inner perimeter and an outer perimeter, wherein the grommet is inserted between the head of the needle and the needle support; the inner perimeter being similar in shape as the needle support and the outer perimeter being similar in shape as the needle head.

2. The device according to claim 1, wherein the hollow hand grip is surrounded by a formed hand grip of various materials.

3. The device according to claim 1, wherein a set screw is not present.

4. The device according to claim 1, wherein the controlling means for directing the DC coil uses a pulse width modulation (PWM) circuit to control when the single DC coil is energized.

5. The device according to claim 4, wherein the pulse width is varied as desired by manipulation of a potentiometer.

6. The device according to claim 1, further comprising a power supply.

7. The device according to claim 1, wherein the head of the needle and the needle support are of similar shape.

8. A method for tattooing biological tissue, the method comprising:
  gripping a tattoo device with at least a single hand, the tattoo device being comprised of
    a body support comprised of a substantially planar section and an elevated section;
    a hollow hand grip attached to a bottom side of the planar section, the hollow hand grip having at least a first opening and a second opening, each opening opposed and connected to one another;
    a single DC coil on a topside of the planar section;
    a controlling means connected to the DC coil for controlling the direction of current through the DC coil, and determining and setting the speed and strength at which the current through the DC coil changes direction;
    an armature bar connected to the body support, wherein the armature bar has a first end and a second end, the first end connected to the elevated section of the body support and the second end having a needle support;
    a magnetic flux guide connected to the top side of the planar section and a portion of which is surrounded by the single DC coil;
    a magnet attached to an underside of the armature bar and adjacent to the topside of the single DC coil;
    a needle held at a head by the needle support and directed towards the body support and through the first opening and second opening of the hollow hand grip, wherein the head of the needle and the needle support are of different shape; and
    a grommet having an inner perimeter and an outer perimeter, wherein the grommet is inserted between the head of the needle and the needle support; the inner perimeter being similar in shape as the needle support and the outer perimeter being similar in shape as the needle head;
  connecting the tattoo device with a power source to allow for energizing the DC coil and driving of the needle;
  contacting the needle of the tattoo device with ink; and
  manipulating the tattoo device such that the needle contacts and pierces the biological tissue desired to be tattooed.

9. The method according to claim 8, wherein the hollow hand grip is surrounded by a formed hand grip of various materials.

10. The method according to claim 8, wherein a set screw is not present.

11. The method according to claim 8, wherein the controlling means for directing the DC coil uses a pulse width modulation (PWM) circuit to control when the single DC coil is energized.

12. The method according to claim 11, wherein the pulse width is varied as desired by manipulation of a potentiometer.

* * * * *